United States Patent
Jordan et al.

(10) Patent No.: US 8,209,811 B2
(45) Date of Patent: Jul. 3, 2012

(54) DISPOSABLE FLOOR MAT CARRYING SANITIZER

(75) Inventors: David B. Jordan, Sandy, UT (US); Steven J. Etheridge, Sandy, UT (US)

(73) Assignee: David B. Jordan, Sandy, UT (US)

( * ) Notice: Subject to any disclaimer, the term of this patent is extended or adjusted under 35 U.S.C. 154(b) by 9 days.

(21) Appl. No.: 12/815,582

(22) Filed: Jun. 15, 2010

(65) Prior Publication Data

US 2010/0316528 A1 Dec. 16, 2010

Related U.S. Application Data

(60) Provisional application No. 61/268,539, filed on Jun. 15, 2009.

(51) Int. Cl.
*A47L 23/26* (2006.01)
*A61L 2/18* (2006.01)

(52) U.S. Cl. .............................. 15/215; 422/292; 422/28

(58) Field of Classification Search .................... 15/215; 422/28, 37, 292
See application file for complete search history.

(56) References Cited

U.S. PATENT DOCUMENTS

| | | | | |
|---|---|---|---|---|
| 1,992,648 | A * | 2/1935 | Browne | 604/293 |
| 2,604,377 | A * | 7/1952 | Eames | 15/105 |
| 3,253,293 | A | 5/1966 | George et al. | |
| 4,125,656 | A | 11/1978 | Creamer | |
| 4,285,075 | A | 8/1981 | Nelson | |
| 4,328,275 | A | 5/1982 | Vargo | |
| 4,609,580 | A | 9/1986 | Rockett et al. | |
| 4,644,592 | A | 2/1987 | Small | |
| 4,876,135 | A | 10/1989 | McIntosh | |
| 5,028,468 | A | 7/1991 | Taylor | |
| 5,297,309 | A * | 3/1994 | Rotoli | 15/104.92 |
| 5,383,570 | A | 1/1995 | Gordon | |
| 6,200,661 | B1 | 3/2001 | Daniels et al. | |
| 6,295,658 | B1 | 10/2001 | Jenkins | |
| 6,815,379 | B2 | 11/2004 | Nomura | |
| D543,406 | S | 5/2007 | Asack et al. | |
| D552,910 | S | 10/2007 | Connor | |
| 7,553,532 | B2 | 6/2009 | Turner et al. | |
| 2002/0031634 | A1* | 3/2002 | Staal | 428/71 |
| 2005/0160549 | A1* | 7/2005 | Dean | 15/215 |
| 2005/0163678 | A1* | 7/2005 | Clawson et al. | 422/186.07 |
| 2009/0081911 | A1 | 3/2009 | Yang | |

(Continued)

FOREIGN PATENT DOCUMENTS

JP 2003033419 A * 2/2003

(Continued)

OTHER PUBLICATIONS

English Abstract for JP 2003033419 A, inventor: Takamori, published: Feb. 2003.*

(Continued)

*Primary Examiner* — Sean E Conley

(57) ABSTRACT

A disposable mat that carries a sanitizer and is sized and shaped to be positioned on a floor and enables a user to stand upon the mat without directly contacting the floor. The mat may have a toe fold formed in or attached to the front portion of the mat, which toe fold forms an envelope that is closed on at least three sides and allows a user to insert their toes into the envelope. The mat may also be separable along an approximate midline of the disposable mat.

11 Claims, 5 Drawing Sheets

U.S. PATENT DOCUMENTS

2010/0296970 A1* 11/2010 Trimarco et al. ............... 422/37

FOREIGN PATENT DOCUMENTS

| JP | 03095987 U9 | 6/2003 |
| JP | 2004-065885 A | 3/2004 |
| JP | 03115172 U9 | 9/2005 |
| KR | 10-2005-0096269 A | 10/2005 |
| WO | WO 2006/049478 | 5/2006 |

OTHER PUBLICATIONS

Derwent Abstract for KR 2005117179 A, inventor: Shin, published Dec. 2005.*

* cited by examiner

DISPOSABLE FLOOR MAT CARRYING SANITIZER

PRIORITY CLAIM

Priority is claimed to copending U.S. Provisional Patent Application Ser. No. 61/268,539, filed Jun. 15, 2009, which is hereby incorporated herein by reference.

BACKGROUND OF THE INVENTION

1. Field of the Invention

The present invention relates generally to products for personal hygiene and sanitation. More particularly, the present invention relates to products for preventing someone's bare feet from contacting floor surfaces by providing a sanitary area for someone to place their bare feet.

2. Related Art

Many people are concerned about sanitation and personal hygiene, especially when they visit public places. Bacteria, fungus and viruses left by others or allowed to grow due to a lack of consistent cleaning create a real and serious concern for many people that visit public places. These contaminants may be found on numerous surfaces, and are commonly found on the floor. Certain floor surfaces may be considered even more problematic than others, and are particularly troublesome for people not wearing coverings on their feet.

For example, the floors in gymnasium locker rooms and hotel rooms are public places that many people visit frequently, and may often walk about in their bare feet. Such places create a serious concern for people in that their feet may become contaminated with a bacteria, fungus, or virus that is left behind by someone else and/or not cleansed properly. As a result of these concerns, some people have developed a variety of techniques to allow them to change their clothes without having their bare feet touch the floor. Some people may stand on a chair or bench while trying to change clothes. Others may stand on a separate towel or other article of their own clothing. Others may try to stand with one foot inside a pant leg while they try to balance or hop as they position their other foot into the other pant leg. None of these options is particularly dignified, nor are they especially sanitary.

While there are numerous products available intending to help someone maintain their personal hygiene in relation to their hands, the number of products specially designed for protecting a person's bare feet are limited.

SUMMARY OF THE INVENTION

In accordance with one aspect of the invention, a disposable floor mat is provided that carries a sanitizer and is sized and shaped to be positioned on a floor so that a user can stand in bare feet without being in direct contact with the floor is provided. The mat may be a flexible, durable, light weight material that is easily disposable after a single use. The mat may be sized to accommodate any individual, including large, adult athletes or small children. The sanitizer used with the mat may be any compound or substance that may function as an anti-bacterial, anti-viral, or anti-fungal agent, such as an alcohol.

In accordance with another aspect of the invention, the mat may include a fold at the top of the mat that creates an envelope or pocket where a user may place their toes, thus allowing additional protection to the user's toes and some possible cleaning on and between the user's toes. The fold may be loose or attached to the mat. The fold may be attached to the mat in a manner that provides one envelope or pocket, or two or more envelopes or pockets. When the fold creates two pockets, a user may place each set of toes in one of the two pockets. Additionally, the mat may be designed to be separable along the approximate midline of the mat. When the mat is separated into two distinct mats, it may function simply as two separate mats, or in one embodiment, as two separate "slippers" for use with each foot.

Additional features and advantages of the invention will be apparent from the detailed description which follows, taken in conjunction with the accompanying drawings, which together illustrate, by way of example, features of the invention.

DETAILED DESCRIPTION

Figure 1:
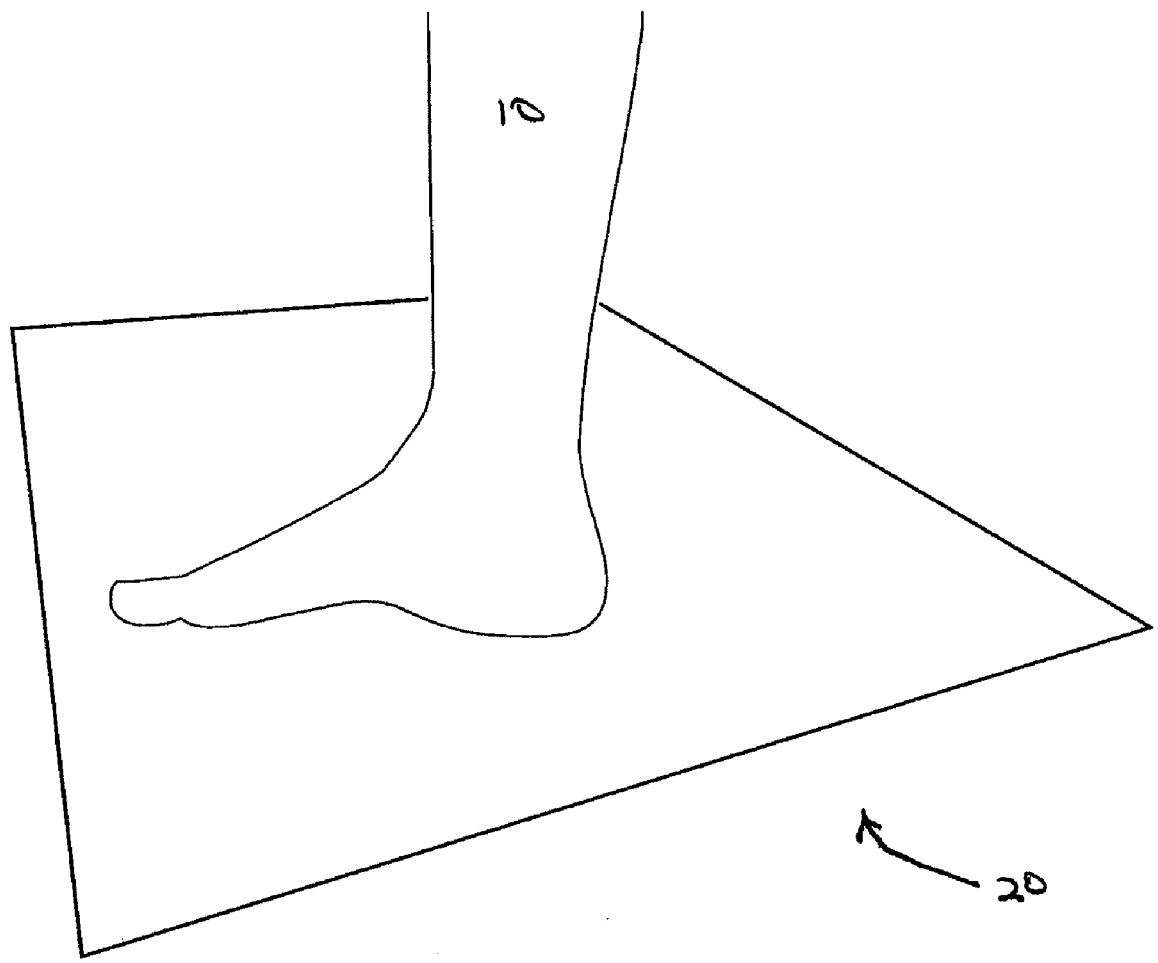
FIG. 1 is a perspective view of a disposable floor mat with a user's bare foot positioned upon the mat.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

As generally illustrated in FIG. 1, in accordance with one aspect, the present invention provides a user with a disposable floor mat 20 that carries a sanitizer or disinfectant. The disposable floor mat 20 is sized and shaped to be positioned on a floor surface such that a user can stand upon (e.g., place or position his or her feet 10 upon) the mat 20 without contacting the floor surface. The disposable floor mat 20 can be of any size that is convenient for a user to stand upon, including adults and children. The disposable floor mat can be flexible and can be formed of a variety of natural or synthetic material that will provide the desired strength and durability while maintaining the disposable nature of the mat 20. For example and not by way of limitation, the disposable floor mat 20 can be comprised of cellulose, cotton, paper, plant fiber, rayon, spun lace, or other textiles, or any combination thereof. The mat 20 may also be formed from products that are biodegradable, providing an environmentally friendly mat.

The sanitizer or disinfectant carried by the disposable floor mat 20 can be a variety of substances that aid in promoting sanitation and personal hygiene, such as an anti-fungal, anti-bacterial, and/or anti-viral substance. The sanitizer may be an alcohol, such as ethyl alcohol, ethanol, isopropanol, and/or a variety of other antiseptic compounds. The sanitizer may be an aldehyde, such as formaldehyde or glutaraldehyde and/or a variety of other fungicidal compounds. The sanitizer may be an oxidizing agent such as sodium hypochlorite, chlorine dioxide, or hydrogen peroxide. The sanitizer may include a silver solution with colloidal silver. The sanitizer may be a phenolic such as phenol or thymol. The sanitizer may also include combinations of these compounds. The sanitizer can be carried in the mat 20 alone or in combination with other compounds, such as a moisturizer.

The disposable floor mat 20 can also carry a moisturizer for delivery to a user's foot or feet. The moisturizer may be any compound that helps protect or maintain or improve a user's skin. For example, the moisturizer may include artificial or natural oils, emollients, humectants, lubricants, etc. The moisturizer may be aloe vera extract, propylene glycol, or any other suitable moisturizer. The sanitizer and/or the moisturizer can be added to the disposable mat in a variety of manners. In one embodiment, the sanitizer and/or the moisturizer are applied primarily to exposed surfaces of the mat. In another embodiment, the sanitizer and/or the moisturizer are at least partially impregnated within the mat (e.g., the mat is at least partially saturated with the sanitizer and/or the moisturizer). The sanitizer and/or moisturizer can be applied to the mat separately, or they can be combined into a single compound that is applied to the mat.

The disposable floor mat 20 can include a membrane layer (not pictured) positioned on the side of the mat 20 that is designed to be placed into contact with the floor surface. The membrane layer can function as additional layer of protection from contact with the floor, and can aid in limiting or preventing the sanitizer from migrating out of or away from the mat 20. The membrane layer may be composed of a polyvinyl or polyurethane substance, or any substance capable of providing the intended function. In one embodiment, the membrane includes a liquid barrier material that both prevents sanitizer from migrating from the mat, and prevents water or other liquids on the floor surface from being absorbed by the mat.

Figure 2:
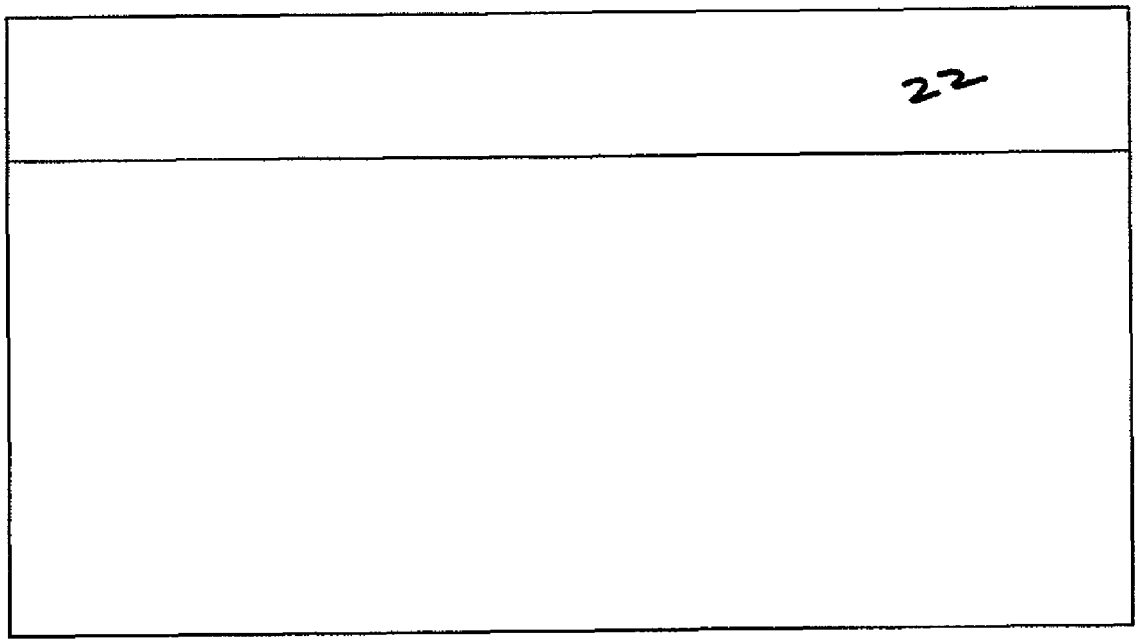
FIG. 2 is a top view of a disposable floor mat having a toe fold formed therein or attached thereto.
Figure 2:

As shown in FIG. 2, the disposable floor mat 20 may also be configured to have a toe fold 22 positioned at the top of the mat 20. The toe fold 22 may be essentially an extension of the mat that can be folded up and over on itself in such a manner that would allow a user to place his or her toes between the mat 20 and the toe fold 22. In one embodiment, the toe fold 22 is not attached to the mat 20 and is closed on only one side. In another embodiment, as shown by example in FIGS. 3 and 4, the toe fold 22 is attached (via stitching or bonding line 24) to the mat 20 on each side of the toe fold 22. In this manner, the toe fold creates an envelope 26 or pocket where a user can position his or her toes between the mat 20 and the toe fold 22. The resulting envelope 26 or pocket can be closed on three sides in a manner that still allows a user 10 to position his or her toes between the mat 20 the toe fold 22.

Figure 4:
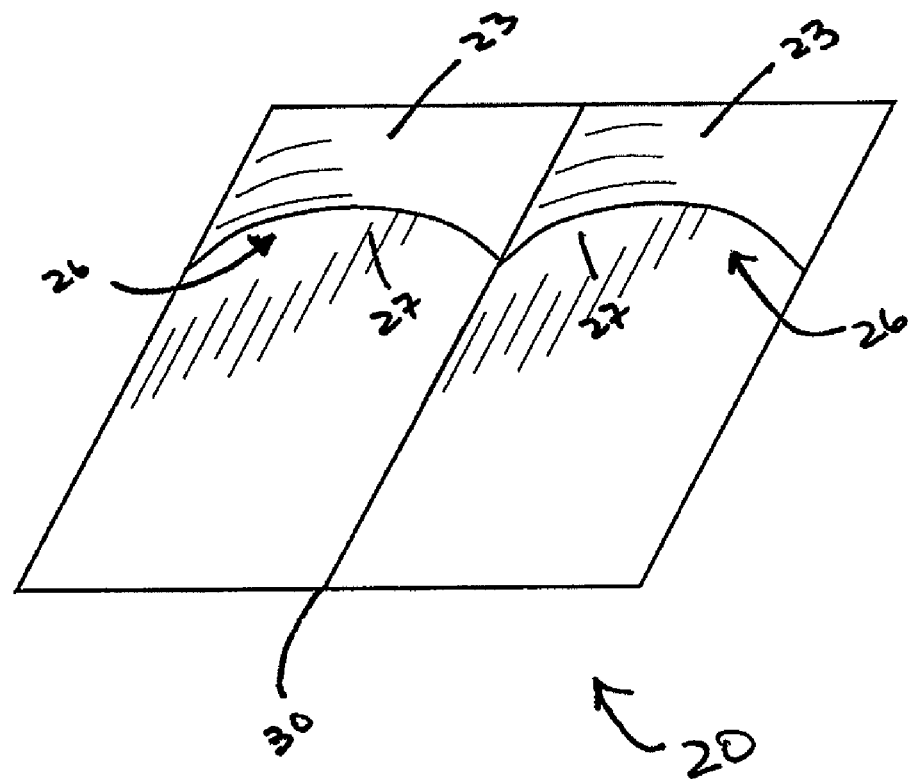
FIG. 4 is a perspective view of a disposable floor mat showing the approximate midline of the mat and having a toe fold that forms a pair of envelopes.

As shown in FIG. 4, the envelope 26 or pocket formed in this manner can include a lower section 27 that is a portion of the mat to be positioned directly over the floor, and an upper section 23 that is formed primarily by the toe fold 22. Thus, a user can position his or her toes between the upper 23 and lower 27 sections of the envelope 26.

Figure 5:
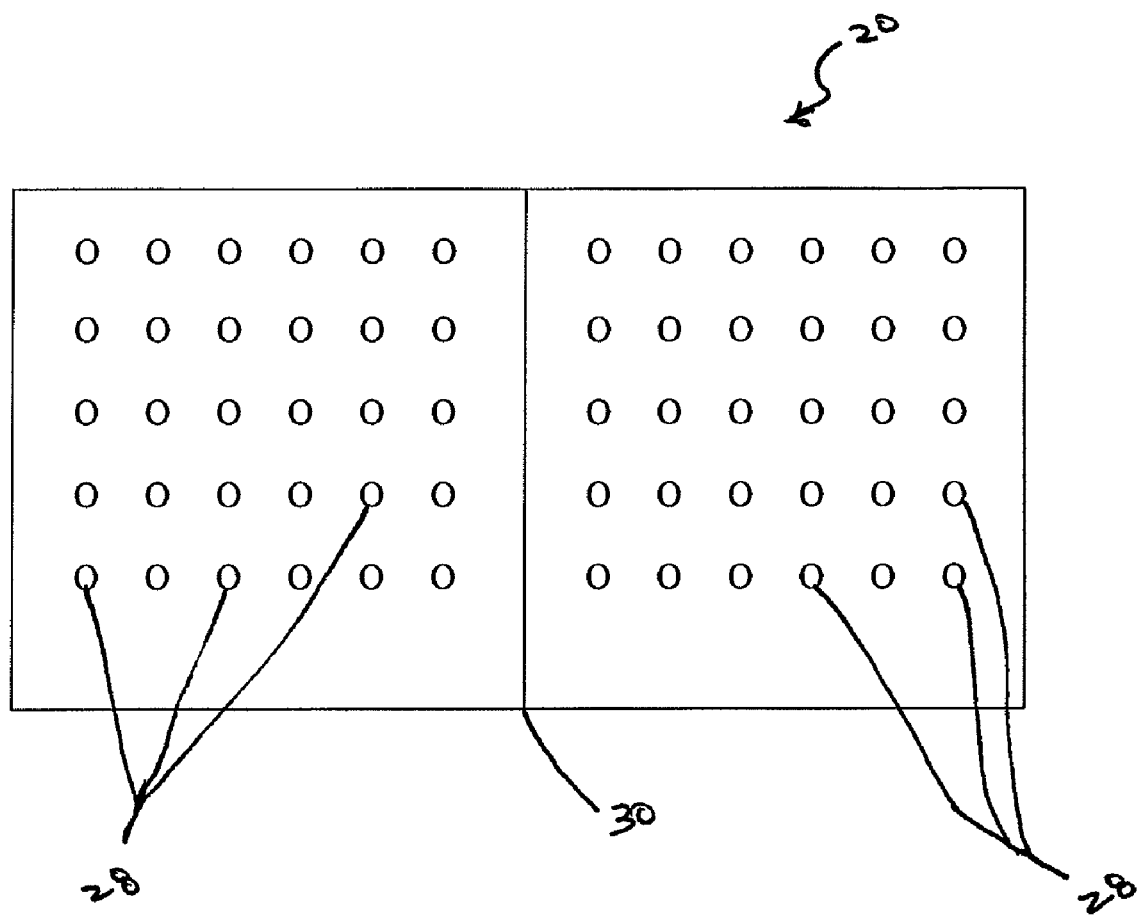
FIG. 5 is a bottom view of a disposable floor mat having non-slip pads applied thereto.

As shown in FIG. 5, the disposable floor mat 20 can also include a plurality of non-slip pads 28 applied on the underside of the mat 20 (e.g., the side intended to be placed into contact with the floor). The non-slip pads 28 help prevent the mat 20 from moving while a user is standing on the mat, particularly when the user is moving while standing on the mat 20, for example, when a user is changing his or her clothes while standing on the mat. The non-slip pads 28 can be composed of any compound or substance that can help increase friction between the floor and the mat 20. For example, the non-slip pads 28 can be composed of an elastomer, rubber, vinyl, or any non-slip textile finishing compound.

The disposable floor mat 20 can also be separable along an approximate midline 30 of the mat 20. The mat can include a perforation line or similar structure along the approximate midline 30 of the mat 20 that can extend from the front of the mat to the rear of the mat. In this manner, the mat 20 can be readily separable by the user into two distinct mats. Moreover, the perforation or apertures can be applied in those embodiments of the mat that include the toe fold 22. In this aspect of the invention, the perforation serves to also render the toe fold 22 separable into two distinct envelopes.

Figure 3:
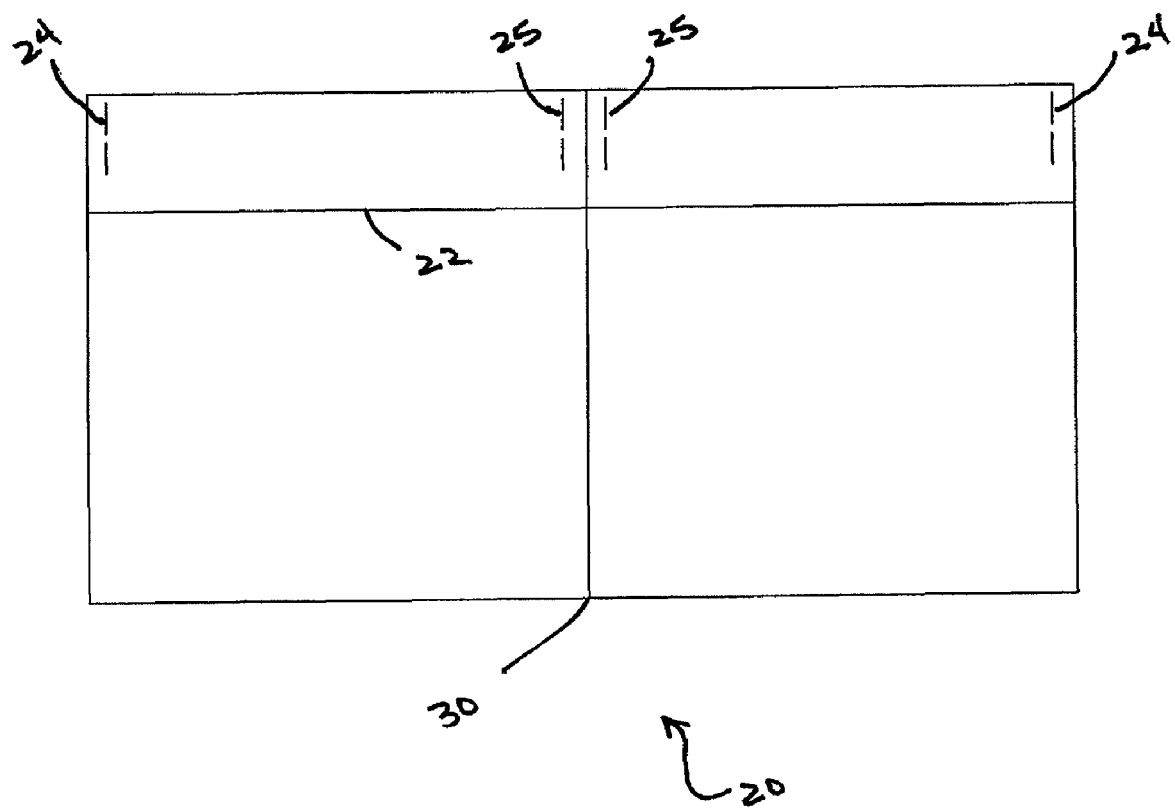
FIG. 3 is a top view of a disposable floor mat showing the approximate midline of the mat and having a toe fold that is formed in or attached to the mat.

In one embodiment of the invention, best appreciated from FIGS. 3 and 4, the disposable floor mat 20 may have a toe fold 22 that is attached to the mat 20 in at least four places, two attachments 24 at each edge of the toe fold 22 and two additional attachments 25 on each side of the approximate midline 30 of the mat 20. In this manner, the mat 20 can provided two distinct envelopes 26 or pockets that are each closed on at least three sides, thereby allowing a user to place at least a portion of one foot 10 in each envelope 26.

Additionally, the perforation or apertures that serve to render the mat 20 separable can be formed along the approximate midline 30 of the mat 20 and between the two toe fold attachments 25 on each side of the approximate midline 30. As a result, a user can position a portion of each foot 10 in each of the two envelopes 26, separate the mat along the approximate midline 30, and thereby have two distinct disposable floor mats, each positioned on one foot. In this manner, the user can be provided with mobility while still maintaining a protective cover beneath each foot, allowing the user to walk about without contacting the floor surface with his or her feet.

As used herein, the term "attachment" is to be understood to refer to any attachment relationship between two parts by which the parts are at least partially restrained relative to one another, even in the absence of fasteners and the like. For example, an attachment may be formed by an adhesive bond or by sewing, stitching, stapling, etc. Note that two attached parts or members may still be moveable relative to one another in one or more directions, while the attaching relationship restrains them from movement in other directions.

While not specifically illustrated in the figures, a logo can be applied to the disposable floor mat 20 in a variety of manners that will allow the logo to be noticeable while the mat 20 is in use. A logo may consist of a design, picture, word, trademark, slogan or a variety of other identifying materials. The logo may be applied to the mat by stitching the logo into the mat, embossing the logo into the mat, stamping the logo into the mat, printing with ink or dye on the mat, and by a variety of other methods that allow the logo to be noticed or read or perceived when the mat is in use. The logo may be applied to a variety of portions on the mat, and formed in or on a variety of different portions of the mat.

It is to be understood that the above-referenced arrangements are illustrative of the application for the principles of the present invention. It will be apparent to those of ordinary skill in the art that numerous modifications can be made without departing from the principles and concepts of the invention as set forth in the claims.

What is claimed is:

1. A floor mat comprising:
a disposable mat, sized and shaped to be positioned on a floor surface to enable a user to stand upon the mat without contacting the floor surface, the disposable mat carrying a sanitizer;

a toe fold formed in or attached to a frontal area of the disposable mat, the toe fold forming an envelope that is closed on at least three sides and includes a portion of the disposable mat on an upper and a lower section of the envelope;

the toe fold is formed in or attached to the disposable mat in a manner that allows the user to position his or her toes between the upper and lower sections of the envelope;

the disposable mat is separable along an approximate midline of the disposable mat; and two disposable mats are formed after separation, each of the two including an envelope that is closed on at least three sides.

2. The floor mat of claim 1, further comprising at least one non-slip pad positioned on the bottom of the disposable mat.

3. The floor mat of claim 1, further comprising a logo applied to the disposable mat.

4. The floor mat of claim 1, wherein the sanitizer includes an alcohol.

5. The floor mat of claim 1, wherein the disposable mat is formed from a biodegradable material.

6. A floor mat comprising:

a disposable mat, sized and shaped to be positioned on a floor surface to enable a user to stand upon the mat without contacting the floor surface, the disposable mat carrying a sanitizer;

a toe fold formed in or attached to a frontal area of the disposable mat, the toe fold forming an envelope that is closed on at least three sides and includes a portion of the disposable mat on an upper and a lower section of the envelope;

the disposable mat being separable along an approximate midline of the disposable mat; and two disposable mats are formed after separation, each of the two including an envelope that is closed on at least three sides.

7. The floor mat of claim 6, further comprising at least one non-slip pad positioned on the bottom of the disposable mat.

8. The floor mat of claim 6, further comprising a logo applied to the disposable mat.

9. The floor mat of claim 6, wherein the sanitizer includes an alcohol.

10. The floor mat of claim 6, wherein the disposable mat is formed from a biodegradable material.

11. A method for protecting a user's feet from contact with a floor surface, comprising:

obtaining a disposable mat carrying a sanitizer and having a toe fold formed in or attached to a frontal area of the disposable mat, the toe fold forming an envelope that is closed on at least three sides and including a portion of the disposable mat on an upper and a lower section of the envelope, the disposable mat being separable along an approximate midline of the disposable mat;

positioning the disposable mat on a floor surface;

positioning the user's bare feet on the disposable mat such that the user's toes are at least partially within the envelope and such that the user's feet are protected from contact with the floor surface;

separating two portions of the disposable mat to provide foot coverings that can cover the user's feet while he or she walks; and disposing of the disposable mat after use.

* * * * *